US007916835B2

(12) United States Patent
Abe et al.

(10) Patent No.: US 7,916,835 B2
(45) Date of Patent: Mar. 29, 2011

(54) X-RAY IMAGING APPARATUS, CONTROL METHOD FOR X-RAY IMAGING APPARATUS, PROGRAM, AND STORAGE MEDIUM

(75) Inventors: Masahiro Abe, Yamato (JP); Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 110 days.

(21) Appl. No.: 12/251,138

(22) Filed: Oct. 14, 2008

(65) Prior Publication Data

US 2009/0103685 A1 Apr. 23, 2009

(30) Foreign Application Priority Data

Oct. 23, 2007 (JP) ................................ 2007-275668

(51) Int. Cl.
*G01N 23/083* (2006.01)
*H05G 1/64* (2006.01)
*A61B 6/08* (2006.01)

(52) U.S. Cl. .......... 378/62; 378/98.8; 378/205; 378/206

(58) Field of Classification Search .................... 378/62, 378/91, 98.8, 145, 204–207, 210, 17, 19, 378/20, 167–170, 189, 191, 98, 113–116

See application file for complete search history.

(56) References Cited

U.S. PATENT DOCUMENTS

| 4,178,508 | A * | 12/1979 | Hotta et al. ..................... 378/97 |
| 6,106,152 | A * | 8/2000 | Thunberg ...................... 378/205 |
| 6,449,337 | B1 * | 9/2002 | Honda et al. .................. 378/117 |
| 6,549,609 | B1 * | 4/2003 | Iinuma et al. ................. 378/150 |
| 7,726,879 | B2 * | 6/2010 | Abe et al. ...................... 378/206 |
| 2004/0105526 | A1 * | 6/2004 | Zhang et al. .................. 378/205 |
| 2005/0069091 | A1 * | 3/2005 | Arakawa ....................... 378/205 |
| 2006/0109958 | A1 * | 5/2006 | Ertel et al. .................... 378/205 |
| 2009/0086926 | A1 * | 4/2009 | Wang et al. ................... 378/206 |

FOREIGN PATENT DOCUMENTS

JP 03-251231 11/1991

* cited by examiner

*Primary Examiner* — Edward J Glick
*Assistant Examiner* — Anastasia Midkiff
(74) *Attorney, Agent, or Firm* — Cowan, Liebowitz & Latman, P.C.

(57) ABSTRACT

An X-ray imaging apparatus includes an X-ray collimator control unit which controls an X-ray collimator shape, an X-ray irradiation unit which irradiates X-rays in accordance with the X-ray collimator shape, an X-ray imaging unit which receives the irradiated X-rays and acquires a radiograph, a perpendicularity determination unit which determines, on the basis of the comparison between the X-ray collimator shape and the radiograph, whether the X-ray irradiation direction of the X-ray irradiation unit is perpendicular to a light-receiving surface by which the X-ray imaging unit receives the X-rays, and an irradiation control unit which controls X-ray irradiation by the X-ray irradiation unit on the basis of the determination result obtained by the perpendicularity determination unit.

8 Claims, 4 Drawing Sheets

US 7,916,835 B2

X-RAY IMAGING APPARATUS, CONTROL METHOD FOR X-RAY IMAGING APPARATUS, PROGRAM, AND STORAGE MEDIUM

BACKGROUND OF THE INVENTION

1. Field of the Invention

The present invention relates to an X-ray imaging technique.

2. Description of the Related Art

Conventionally, an X-ray imaging apparatus used in a hospital or the like uses a cassette. After an exposed cassette is developed, the developed film is interpreted by using an observation device called a film viewer. With the recent advances in computer technology, it is possible to perform a series of operations from imaging to interpretation with digital images. Use of a portable FPD (Flat Panel Detector) instead of a conventional cassette can implement digital image processing. For example, the above conventional technique is disclosed in Japanese Patent Laid-Open No. 3-251231.

When general X-ray imaging with a cassette is to be performed, the cassette is set at a predetermined position. A subject is then placed on the cassette, and X-ray imaging is performed. In this case, it is necessary to perform positioning such that the central axis of X-ray irradiation from an X-ray tube becomes perpendicular to the light-receiving surface of the cassette.

In the method using a cassette, however, an angle detection result cannot be used for X-ray control during imaging.

SUMMARY OF THE INVENTION

The present invention has been made in consideration of the problems in the prior art described above, and has as its object to provide an X-ray imaging technique which can control X-ray irradiation on the basis of a detection result on the angle defined by X-rays irradiated from an X-ray generation unit and an X-ray imaging unit during X-ray radioscopy.

According to one aspect of the present invention, there is provided an X-ray imaging apparatus comprising:

an X-ray collimator control unit adapted to control an X-ray collimator shape;

an X-ray irradiation unit adapted to irradiate X-rays in accordance with the X-ray collimator shape;

an X-ray imaging unit adapted to receive the X-rays irradiated by the X-ray irradiation unit and acquire a radiograph on the basis of the X-rays;

a perpendicularity determination unit adapted to determine, on the basis of a comparison between the X-ray collimator shape and the radiograph, whether an X-ray irradiation direction of the X-ray irradiation unit is perpendicular to a light-receiving surface by which the X-ray imaging unit receives the X-rays; and an irradiation control unit adapted to control X-ray irradiation by the X-ray irradiation unit on the basis of a determination result obtained by the perpendicularity determination unit.

According to another aspect of the present invention, there is provided a control method for an X-ray imaging apparatus, the method comprises:

an X-ray collimator control step of controlling an X-ray collimator shape;

an X-ray irradiation step of irradiating X-rays in accordance with the X-ray collimator shape;

a radiograph capturing step of receiving the X-rays irradiated in the X-ray irradiation step and acquiring a radiograph on the basis of the X-rays;

a perpendicularity determination step of determining, on the basis of a comparison between the X-ray collimator shape and the radiograph, whether an X-ray irradiation direction of the X-ray irradiation unit is perpendicular to a light-receiving surface by which the radiograph capturing unit receives the X-rays; and an irradiation control step of controlling X-ray irradiation in the step of irradiating X-rays on the basis of a determination result obtained by the perpendicularity determination unit.

According to the present invention, it is possible to control X-ray irradiation on the basis of the result of perpendicularity determination, that is, determining whether the irradiation direction of X-rays irradiated from the X-ray generation unit is perpendicular to the light-receiving surface of the X-ray imaging unit during X-ray radioscopy.

Assume that it is determined on the basis of perpendicularity determination result during X-ray radioscopy that irradiated X-rays are not perpendicular to the light-receiving surface of the X-ray imaging unit. In this case, performing control to stop X-ray irradiation makes it possible to prevent excessive irradiation and leakage of X-rays.

Further features of the present invention will become apparent from the following description of exemplary embodiments with reference to the attached drawings.

DESCRIPTION OF THE EMBODIMENTS

The preferred embodiments of the present invention will be described exemplarily in detail below with reference to the accompanying drawings. The constituent elements described in these embodiments are merely examples. The technical range of the present invention is defined by the claims, but is not limited by each embodiment to be described below.

First Embodiment

Figure 1:
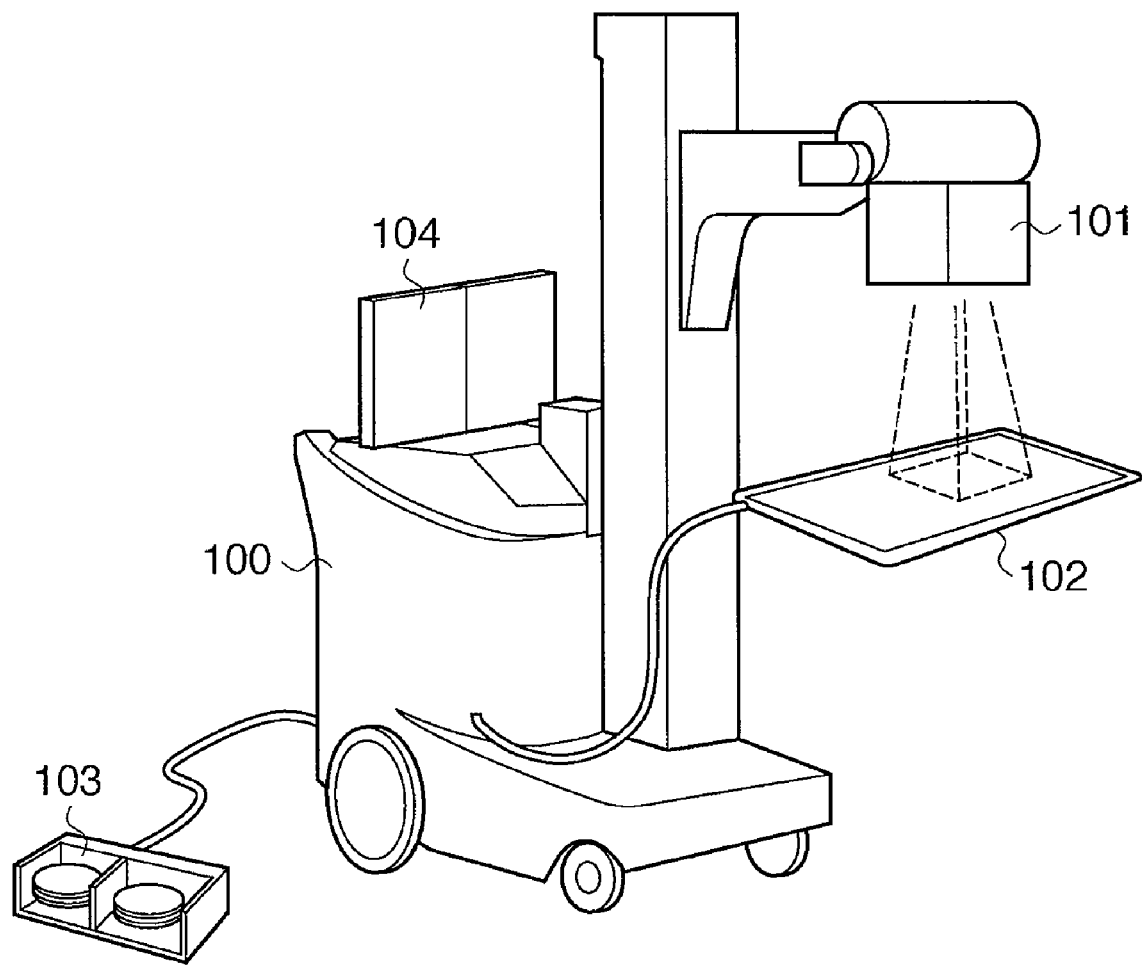
FIG. 1 is a view exemplarily showing the outer appearance of an X-ray imaging apparatus according to an embodiment of the present invention.

FIG. 1 is a view exemplarily showing the outer appearance of an X-ray imaging apparatus according to the first embodiment of the present invention. The X-ray imaging apparatus can be moved by a nursing cart 100 including a moving mechanism, and comprises an X-ray generation unit 101, an X-ray sensor 102, a foot pedal 103, and a display unit 104. The housing of the nursing cart 100 incorporates a controller for controlling the X-ray imaging apparatus. The controller can control X-ray irradiation by the X-ray generation unit 101 on the basis of radiograph signals acquired by the X-ray sensor 102, operation inputs from the foot pedal 103, and the like.

The X-ray generation unit 101 includes a mechanism for generating X-rays, which comprises an X-ray tube, an X-ray collimator, and the like. The X-ray sensor 102 is a sensor which receives X-rays irradiated by the X-ray generation unit 101, and acquires a radiograph signal. The radiograph signal acquired by the X-ray sensor is input to the controller.

The foot pedal 103 is an input device for instructing the controller to irradiate X-rays or stop irradiation. The controller can control irradiation of X-rays and the stoppage of X-ray irradiation by controlling the X-ray generation unit 101 on the basis of inputs from the foot pedal 103.

The display unit 104 comprises a general monitor such as a CRT or liquid crystal display, and displays image data, a GUI (Graphical User Interface), and the like on a screen. The controller can execute display control to display an X-ray imaging result as image data on the display unit 104.

Note that the X-ray imaging apparatus comprises general input devices such as a keyboard and mouse (not shown) in addition to the foot pedal 103. The user can input instructions to the controller via the input devices such as the keyboard and mouse so as to operate and control the X-ray imaging apparatus.

Figure 2:
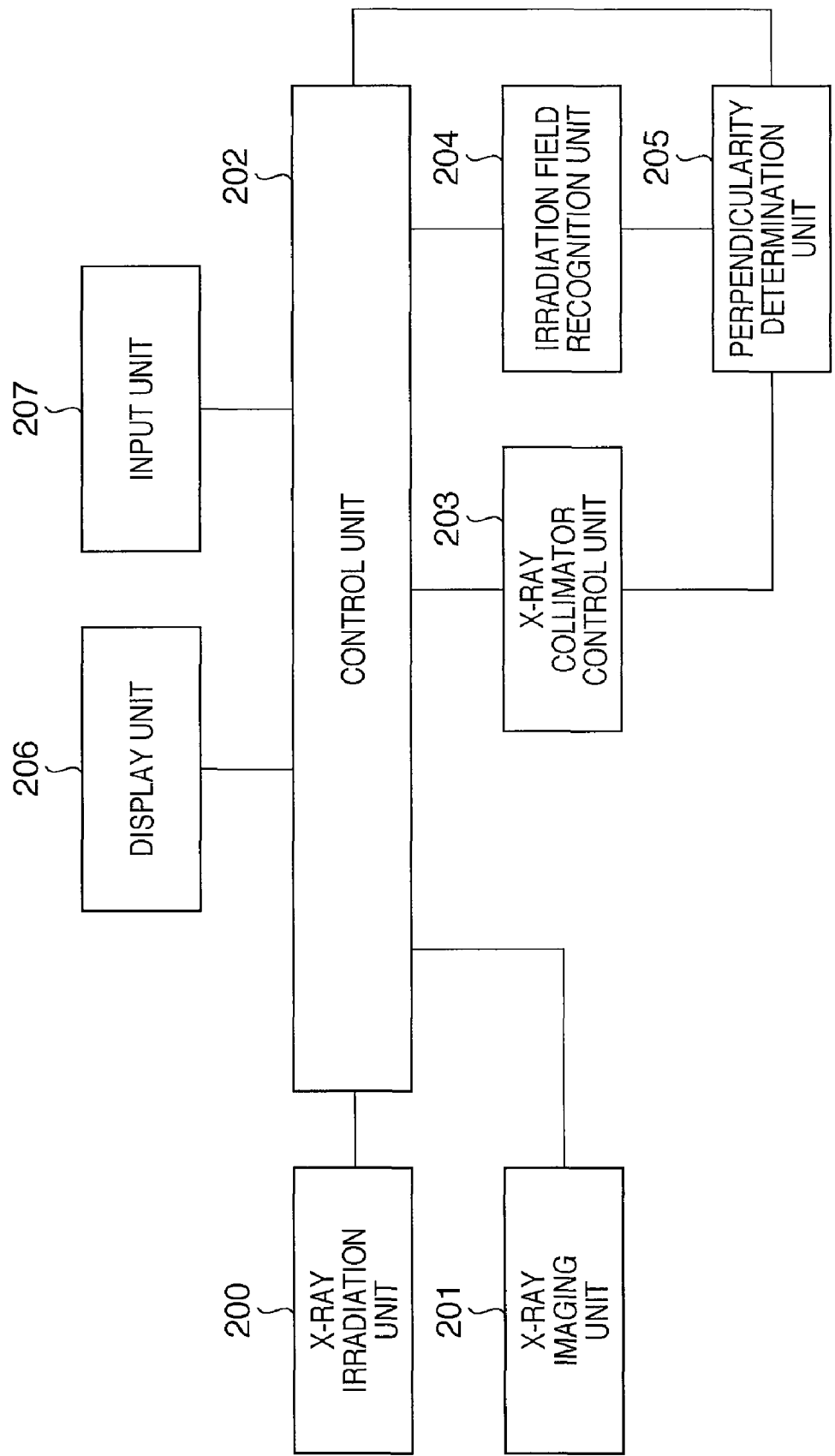
FIG. 2 is a block diagram showing a functional arrangement of the X-ray imaging apparatus according to the embodiment of the present invention.

The functional arrangement of the X-ray imaging apparatus will be described next. FIG. 2 is a block diagram showing the functional arrangement of the X-ray imaging apparatus according to the first embodiment of the present invention.

An X-ray irradiation unit 200 corresponds to the functional arrangement of the X-ray generation unit 101 in FIG. 1. The X-ray irradiation unit 200 can generate X-rays and irradiate the X-rays to a subject. An X-ray imaging unit 201 corresponds to the functional arrangement of the X-ray sensor 102, and can acquire a radiograph (X-ray signal) on the basis of received X-rays.

A control unit 202 receives an imaging start (irradiation start) instruction addressed to the X-ray irradiation unit 200 and image data from the X-ray imaging unit 201, and can perform overall control on the X-ray imaging apparatus. In this case, the control unit 202 functions as an irradiation control means for controlling X-ray irradiation. The control unit 202 implements the functional arrangement of the controller housed in the housing of the nursing cart 100.

The control unit 202 includes a CPU (not shown) for executing control on the X-ray imaging apparatus, a memory (not shown) such as a ROM which stores programs executed by the CPU, and a memory (not shown) such as a RAM functioning as a work area of the CPU.

An X-ray collimator control unit 203 is a control unit which controls an X-ray collimator provided for the X-ray irradiation unit 200. The X-ray collimator control unit 203 can control an X-ray collimator shape. An irradiation field recognition unit 204 is a recognition unit which recognizes an X-ray region irradiated to the X-ray sensor 102. The irradiation field recognition unit 204 has a function of discriminating a portion irradiated with X-rays and a portion irradiated with no X-rays on the surface of the X-ray sensor 102 by image processing.

A perpendicularity determination unit 205 compares the X-ray collimator shape managed by the X-ray collimator control unit 203 with the irradiated region discriminated by the irradiation field recognition unit 204, and determines whether the central axis of irradiated X-rays is perpendicular to the light-receiving surface of the X-ray sensor 102.

Information processing, which is performed by cooperation between the programs stored in the ROM and the like of the control unit 202 and the CPU, implements the above functions of the control unit 202, X-ray collimator control unit 203, irradiation field recognition unit 204, and perpendicularity determination unit 205.

The programs to be used are not limited to those stored in the ROM. For example, a hard disk (not shown) in which programs are installed can be further provided, and each program can be downloaded from the hard disk at the time of execution.

A display unit 206 corresponds to the functional arrangement of the display unit 104 in FIG. 1. The display unit 206 can control the display of the display unit 104 on the basis of the information received from the control unit 202. An input unit 207 corresponds to the functional arrangements of general input devices such as a mouse and keyboard, in addition to the foot pedal 103 in FIG. 1, with which the user issues various operation instructions to the X-ray imaging apparatus.

(Processing Sequence at Time of X-ray Imaging)

Figure 3:
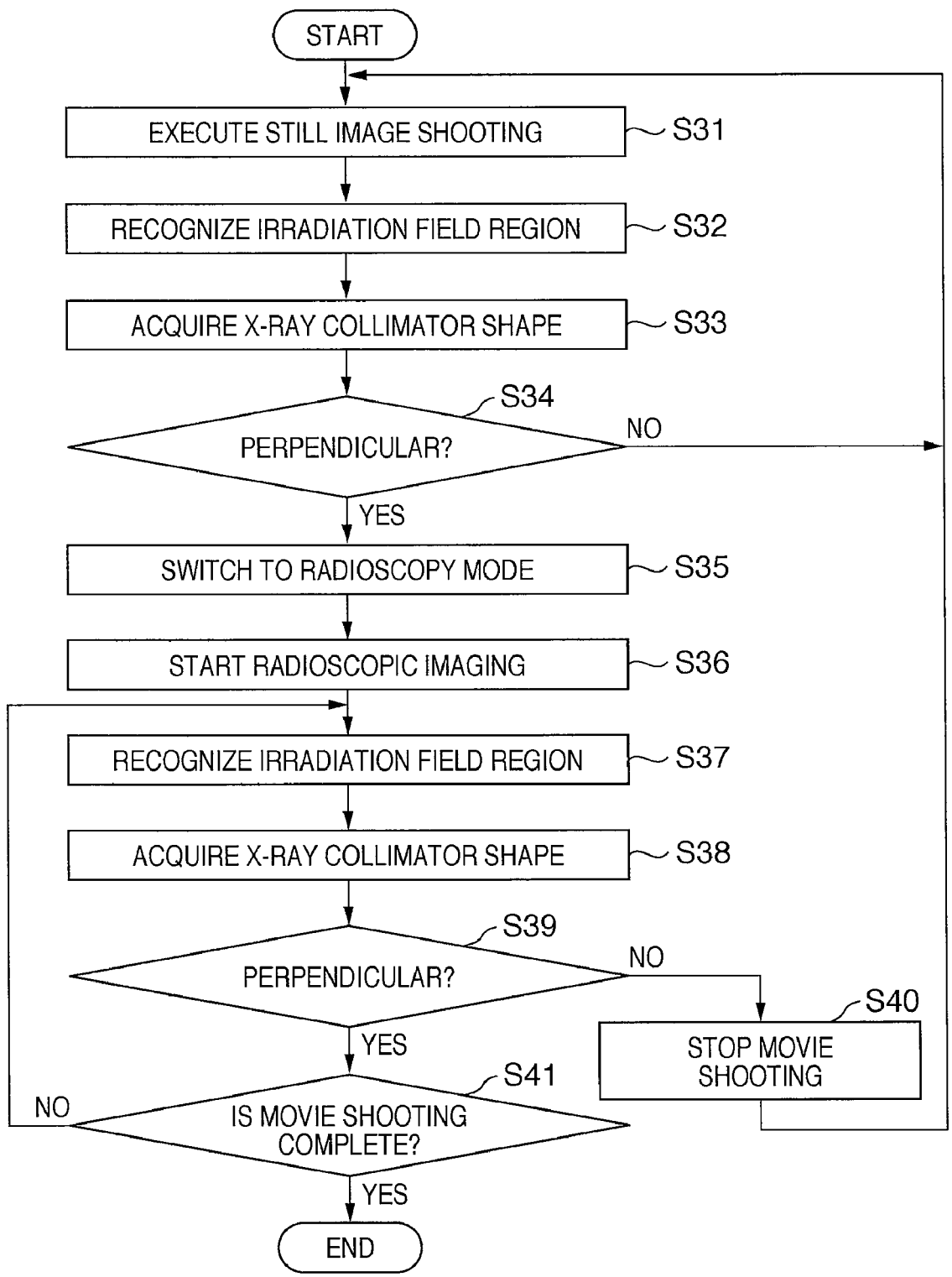
FIG. 3 is a flowchart for explaining a processing sequence at the time of X-ray imaging in the X-ray imaging apparatus according to the embodiment of the present invention.

A processing sequence at the time of X-ray imaging in the X-ray imaging apparatus according to this embodiment will be described next with reference to the flowchart of FIG. 3.

In step S31, the X-ray collimator control unit 203 controls an X-ray collimator shape. The control unit 202 causes the X-ray generation unit 101 to irradiate X-rays to execute still image shooting on the basis of the controlled X-ray collimator shape. In this step, the control unit 202 performs imaging without placing any subject.

In step S32, the irradiation field recognition unit 204 determines whether the irradiated region (X-ray irradiation field) of X-rays received by the X-ray sensor 102 falls within the light-receiving surface.

In step S33, the perpendicularity determination unit 205 acquires an X-ray collimator shape from the X-ray collimator control unit 203.

In step S34, the perpendicularity determination unit 205 determines whether the central axis of irradiated X-rays in the irradiation direction (the central axis of X-ray irradiation) is perpendicular to the light-receiving surface of the X-ray sensor 102. Determination of whether the central axis of irradiated X-rays in the irradiation direction (the central axis of X-ray irradiation) is perpendicular to the light-receiving surface of the X-ray sensor 102 will be described later with reference to FIGS. 4A and 4B. If the perpendicularity determination unit 205 determines that the central axis of X-ray irradiation is perpendicular to the light-receiving surface of the X-ray sensor 102 (YES in step S34), the process advances to step S35. In contrast, if the perpendicularity determination unit 205 determines in step S34 that the central axis of X-ray irradiation is not perpendicular to the light-receiving surface of the X-ray sensor 102 (NO in step S34), the process returns to step S31.

In step S35, the X-ray imaging mode is switched from the still image shooting mode to radioscopy mode (movie shooting mode). The user can switch the X-ray imaging mode by operating the input unit 207. In addition, the control unit 202 can automatically switch the X-ray imaging mode upon receiving the determination result in step S34.

Note that in the interval from step S34 to step S36, a patient (subject) as an X-ray imaging target is placed at a predetermined position between the X-ray generation unit 101 and the X-ray sensor 102.

In step S36, radioscopic imaging (X-ray movie shooting) is started under the control of the control unit 202. When the user performs input operation, for example, stepping on the foot pedal 103, an instruction to start X-ray irradiation is input to the control unit 202. Upon receiving the X-ray irradiation start instruction, the control unit 202 controls the X-ray generation unit 101. The X-ray generation unit 101 then starts irradiating X-rays. When radioscopic imaging (X-ray movie shooting) starts, the X-ray sensor 102 receives the X-rays irradiated from the X-ray generation unit 101. The X-ray sensor 102 then transmits image data as a result of X-ray imaging to the control unit 202.

In step S37, the irradiation field recognition unit 204 discriminates a portion irradiated with X-rays and a portion irradiated with no X-rays on the surface of the X-ray sensor 102 during radioscopic imaging (X-ray movie shooting). The discrimination result obtained by the irradiation field recognition unit 204 is input to the control unit 202 and the perpendicularity determination unit 205.

In step S38, the X-ray collimator control unit 203 acquires an X-ray collimator shape during radioscopic imaging (X-ray imaging). The X-ray collimator shape acquired by the X-ray collimator control unit 203 is input to the control unit 202 and the perpendicularity determination unit 205.

In step S39, the perpendicularity determination unit 205 determines, on the basis of the information obtained in steps S37 and S38, whether the central axis of irradiated X-rays in the X-ray irradiation direction (the central axis of X-ray irradiation) is perpendicular to the light-receiving surface of the X-ray sensor 102.

If the perpendicularity determination unit 205 determines in step S39 that the central axis of irradiated X-rays in the X-ray irradiation direction (the central axis of X-ray irradiation) is perpendicular to the light-receiving surface of the X-ray sensor 102 (YES in step S39), the process advances to step S41.

It is determined in step S41 whether movie shooting is complete. If it is determined in step S41 that movie shooting is not complete (NO in step S41), the process returns to step S37. The processing after step S37 is then executed in the same manner as described above. The processing from step S37 to step S39 is continuously executed while the instruction to start X-ray irradiation is input to the control unit 202, for example, while the user keeps stepping on the foot pedal 103 (during radioscopy). If it is determined that movie shooting is complete (YES in step S41), processing is terminated.

If the perpendicularity determination unit 205 determines in step S39 that the central axis of irradiated X-rays (the central axis of X-ray irradiation) is not perpendicular to the light-receiving surface of the X-ray sensor 102 (NO in step S39), the process advances to step S40. The perpendicularity determination unit 205 transmits, to the control unit 202, the determination result indicating that the central axis of X-ray irradiation is not perpendicular to the light-receiving surface of the X-ray sensor 102.

In step S40, the control unit 202 receives, from the perpendicularity determination unit 205, the determination result indicating that the central axis of X-ray irradiation is not perpendicular to the light-receiving surface of the X-ray sensor 102 during movie shooting. Based on the determination result, the control unit 202 controls the X-ray generation unit 101 to stop X-ray irradiation and movie shooting. The X-ray generation unit 101 stops X-ray irradiation under the control of the control unit 202.

Upon receiving, from the perpendicularity determination unit 205, the determination result indicating that the central axis of X-ray irradiation is not perpendicular to the light-receiving surface of the X-ray sensor 102, the control unit 202 inputs the determination result to the display unit 206. The display unit 206 can perform display control to make the display unit 104 display a warning for notifying the user that the central axis of X-ray irradiation is not perpendicular to the light-receiving surface of the X-ray sensor 102. In accordance with the warning displayed on the display unit 104, the user can switch the operation of the foot pedal 103.

When the instruction to irradiate X-rays is not input to the control unit 202, for example, when the foot pedal 103 is restored from the pressed state, the control unit 202 can control the X-ray generation unit 101 to stop X-ray imaging.

(Perpendicularity Determination Method)

Figure 4A:
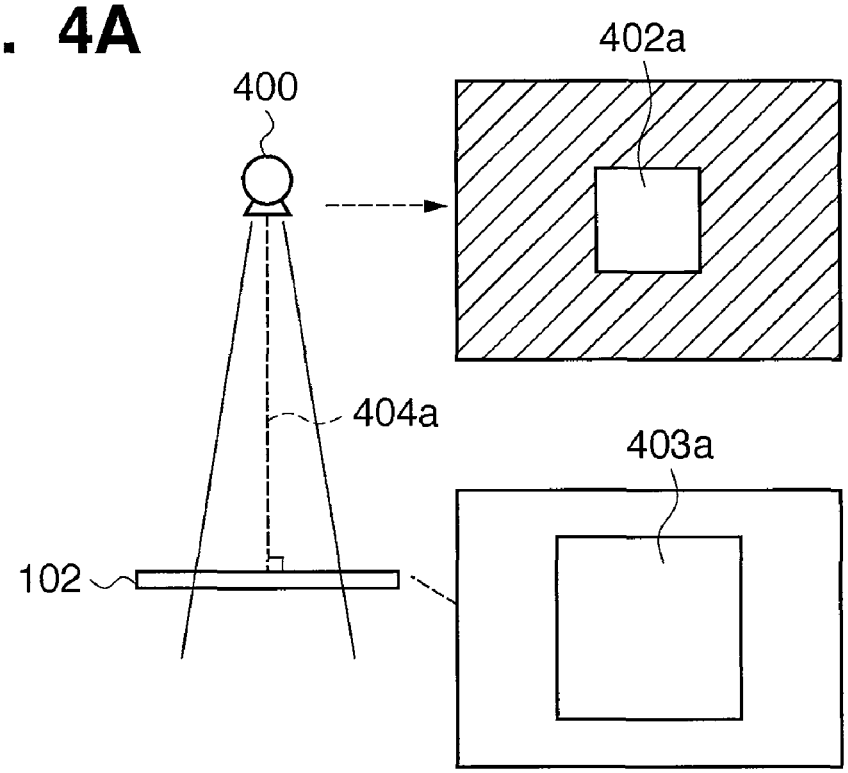
FIGS. 4A and 4B are views schematically showing a case in which the central axis of X-ray irradiation is perpendicular to the light-receiving surface of an X-ray sensor and a case in which the central axis of X-ray irradiation is not perpendicular to the light-receiving surface, respectively.
Figure 4B:
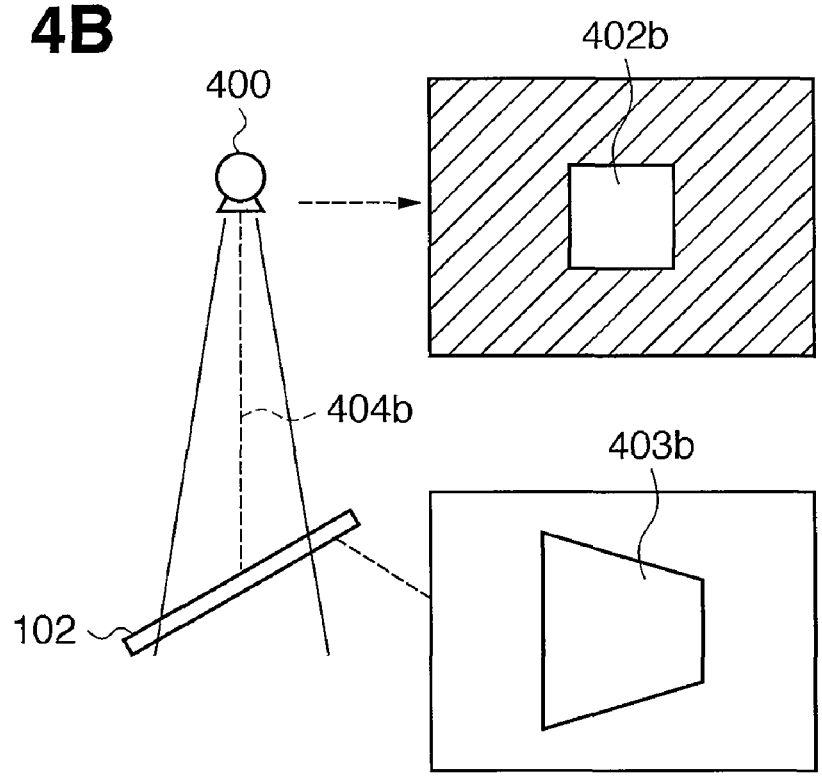

The determination method executed by the perpendicularity determination unit 205 will be described next. This method is a method of determining whether the central axis of irradiated X-rays (the central axis of X-ray irradiation) is perpendicular to the light-receiving surface of the X-ray sensor 102 (perpendicularity). FIG. 4A is a view schematically showing a case in which the central axis of X-ray irradiation is perpendicular to the light-receiving surface of the X-ray sensor 102. FIG. 4B is a view schematically showing a case in which the central axis of X-ray irradiation is not perpendicular to the light-receiving surface of the X-ray sensor 102.

The X-ray generation unit 101 includes an X-ray tube 400 as a constituent element of the X-ray generation unit 101 which generates X-rays. The X-ray collimator control unit 203 controls the X-ray collimator of the X-ray tube 400 to acquire, for example, rectangular X-ray collimator shapes 402a and 402b including squares. Reference numerals 404a and 404b denote the central axes of X-rays irradiated from the X-ray tube 400 (the central axes of X-ray irradiation). When the central axis 404a of irradiated X-rays (the central axis of X-ray irradiation) is perpendicular to the light-receiving surface of the X-ray sensor 102, the irradiation field recognition unit 204 detects a rectangular irradiation field shape 403a similar to the X-ray collimator shape 402a.

If the central axis 404b of irradiated X-rays is not perpendicular to the light-receiving surface of the X-ray sensor 102, the irradiation field recognition unit 204 detects a trapezoidal irradiation field shape 403b. If the X-ray collimator shape 402b is not similar to the irradiation field shape 403b, the perpendicularity determination unit 205 determines that the central axis 404b of X-rays is not perpendicular to the light-receiving surface of the X-ray sensor 102.

In the case of a rectangular collimator shape, the perpendicularity determination unit 205 can calculate the aspect ratio of the collimator shape by inquiring the X-ray collimator control unit 203 of the horizontal opening width and vertical opening width of the collimator shape. Likewise, the perpendicularity determination unit 205 can calculate the aspect ratio of the irradiation field shape acquired by the irradiation field recognition unit 204 and determine the similarity between the X-ray collimator shape and the irradiation field shape by determining whether their aspect ratios coincide with each other. In this case, the irradiation field recognition unit 204 extracts a straight line by general image processing such as Hough conversion to recognize that the irradiation field region is rectangular, and can recognize, from the relationship with the extracted straight line, that the irradiation field shape is rectangular. The extraction of an irradiation area by the irradiation field recognition unit 204 is implemented by image processing and is widely and generally performed in X-ray imaging apparatuses. A description of this extraction processing itself will be omitted in this embodiment.

As described above, according to this embodiment, it is possible to control X-ray irradiation on the basis of a determination result on perpendicularity, that is, determination of whether the irradiation direction of X-rays irradiated from the X-ray generation unit is perpendicular to the light-receiving surface of the X-ray imaging unit, during X-ray radioscopy.

Alternatively, if it is determined, on the basis of a determination result on perpendicularity during X-ray radioscopy, that the irradiation direction of irradiated X-rays is not perpendicular to the light-receiving surface of the X-ray imaging unit, it is possible to prevent excessive irradiation or leakage of X-rays by performing control to stop X-ray irradiation.

Second Embodiment

The first embodiment has exemplified the case in which the X-ray collimator shape is rectangular. When the collimator shape is circular, an irradiation field recognition unit 204 can extract an irradiation field region, but it is more difficult for the unit to recognize that the shape is circular than when the shape is rectangular.

In this case, a perpendicularity determination unit 205 can determine the similarity between the X-ray collimator shape inquired from the X-ray collimator control unit 203 and the irradiation field region extracted by the irradiation field recognition unit 204 by using a template matching technique for image processing. Note that template matching is a technique of detecting the similarity between images, and is widely and generally known in the field of image processing. This template matching is not essential to the present invention, and hence a description of the technique will be omitted.

The perpendicularity determination unit 205 can calculate the similarity between the X-ray collimator shape acquired by the X-ray collimator control unit 203, which is used as a template, and the shape of the irradiation field region extracted by the irradiation field recognition unit 204, which is a target. If the calculated similarity is lower than a given threshold, the perpendicularity determination unit 205 determines that the X-ray collimator shape is not similar to the shape of the irradiation field region.

According to this embodiment, using the template matching technique can cope with various X-ray collimator shapes because the technique can determine the similarities of arbitrary X-ray collimator shapes as well as a circular shape.

Third Embodiment

In the first and second embodiments, perpendicularity to the irradiation direction of X-rays (the central axis of X-ray irradiation) is determined by using the shape of the X-ray irradiation field received by the X-ray sensor 102. The gist of the present invention is not limited to this arrangement. For example, it is possible to determine perpendicularity by providing a sensor for detecting the relative positions and angles of an X-ray tube 400 and X-ray sensor 102. For example, a perpendicularity determination unit 205 can determine the perpendicularity between the irradiation direction of X-rays (the central axis of X-ray irradiation) and the X-ray sensor 102 on the basis of the detection result obtained by detecting the angular relationship between the X-ray tube 400 and the X-ray sensor 102 using an angle sensor.

Other Embodiments

The object of the present invention is implemented even by supplying a computer-readable storage medium storing software program codes for implementing the functions of the above embodiments to a system or apparatus, and causing the computer (or the CPU or MPU) of the system or apparatus to read out and execute the program codes stored in the storage medium.

In this case, the program codes read out from the storage medium implement the functions of the above embodiments by themselves, and the storage medium storing the program codes constitutes the present invention.

As a storage medium for supplying the program codes, a flexible disk, hard disk, optical disk, magnetooptical disk, CD-ROM, CD-R, nonvolatile memory card, ROM, or the like can be used.

The functions of the above embodiments are implemented when the computer executes the readout program codes. Obviously, the functions of the above embodiments are also implemented when the OS (Operating System) running on the computer performs part or all of actual processing on the basis of the instructions of the program codes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-275668, filed Oct. 23, 2007, which is hereby incorporated by reference herein in its entirety.

What is claimed is:

1. An X-ray imaging apparatus comprising:
an X-ray collimator control unit adapted to control an X-ray collimator shape;
an X-ray irradiation unit adapted to irradiate X-rays in accordance with the X-ray collimator shape;
an X-ray imaging unit adapted to receive the X-rays irradiated by said X-ray irradiation unit and acquire a radiograph on the basis of the X-rays and be movable;
a perpendicularity determination unit adapted to determine, on the basis of a comparison between the X-ray collimator shape and the radiograph, whether an X-ray irradiation direction of said X-ray irradiation unit is perpendicular to a light-receiving surface by which said X-ray imaging unit receives the X-rays; and
an irradiation control unit adapted to stop X-ray irradiation by said X-ray irradiation unit on the basis of a determination result obtained by said perpendicularity determination unit,
wherein if said perpendicularity determination unit determines in a still image shooting mode that the X-ray irradiation direction is perpendicular to the light-receiving surface, said irradiation control unit is configured to switch to a movie shooting mode.

2. The apparatus according to claim 1, wherein said perpendicularity determination unit determines that the X-ray irradiation direction is perpendicular to the light-receiving surface when it is determined on the basis of the comparison that the radiograph is similar to the X-ray collimator shape.

3. The apparatus according to claim 1, wherein when receiving, from said perpendicularity determination unit, a determination result indicating that the X-ray irradiation direction is not perpendicular to the light-receiving surface, said irradiation control unit controls said X-ray irradiation unit to stop movie shooting by stopping X-ray irradiation.

4. A control method for an X-ray imaging apparatus, the method comprising:
an X-ray collimator control step of controlling an X-ray collimator shape;
an X-ray irradiation step of irradiating X-rays in accordance with the X-ray collimator shape;
a radiograph capturing step of moving an X-ray imaging unit and receiving the X-rays irradiated in the X-ray irradiation step and acquiring a radiograph on the basis of the X-rays;

a perpendicularity determination step of determining, on the basis of a comparison between the X-ray collimator shape and the radiograph, whether an X-ray irradiation direction of the X-ray irradiation unit is perpendicular to a light-receiving surface by which the radiograph capturing unit receives the X-rays; and an irradiation control step of stopping X-ray irradiation in the step of irradiating X-rays on the basis of a determination result obtained by the perpendicularity determination unit, wherein if it is determined in the perpendicularity determination step in a still image shooting mode that the X-ray irradiation direction is perpendicular to the light-receiving surface, it is configured to switch to a movie shooting mode in the irradiation control step.

5. The method according to claim 4, wherein in the perpendicularity determination step, it is determined that the X-ray irradiation direction is perpendicular to the light-receiving surface when it is determined on the basis of the comparison that the radiograph is similar to the X-ray collimator shape.

6. The method according to claim 4, wherein when a determination result indicating that the X-ray irradiation direction is not perpendicular to the light-receiving surface, which is obtained by processing in the perpendicularity determination step, is received in the irradiation control step, X-ray irradiation is controlled to stop the movie shooting by stopping X-ray irradiation in the irradiation control step.

7. A program which is stored in a computer-readable storage medium and causes a computer to execute a control method for an X-ray imaging apparatus defined in claim 4.

8. A computer-readable storage medium which stores a program defined in claim 7.

* * * * *